United States Patent [19]

Jensen

[11] Patent Number: 5,681,725
[45] Date of Patent: Oct. 28, 1997

[54] PROCESS FOR PRODUCING HEME PROTEINS

[75] Inventor: Ejner Bech Jensen, Virum, Denmark

[73] Assignee: Novo Nordisk A/S, Bagsvaerd, Denmark

[21] Appl. No.: 284,566

[22] PCT Filed: Mar. 16, 1993

[86] PCT No.: PCT/DK93/00094

§ 371 Date: Aug. 9, 1994

§ 102(e) Date: Aug. 9, 1994

[87] PCT Pub. No.: WO93/19195

PCT Pub. Date: Sep. 30, 1993

[30] Foreign Application Priority Data

Mar. 20, 1992 [DK] Denmark .................................. 365/92

[51] Int. Cl.⁶ .............. C12P 19/56; C12P 21/04; C07K 14/795; C07K 14/805
[52] U.S. Cl. .............. 435/78; 435/240.1; 435/320.1; 435/71.1; 530/385; 530/400; 530/412; 536/23.1
[58] Field of Search ................. 530/350, 385, 530/400; 435/69.4, 69.1, 69.6, 70.1, 71.1, 78, 240.1, 320.1, 189, 256.1

[56] References Cited

U.S. PATENT DOCUMENTS

| | | | |
|---|---|---|---|
| 4,340,668 | 7/1982 | Hornby et al. | 435/7 |
| 4,885,249 | 12/1989 | Buston et al. | 435/172.3 |

FOREIGN PATENT DOCUMENTS

| | | |
|---|---|---|
| 0 215 594 | 3/1987 | European Pat. Off. . |
| 0 505 311 | 9/1992 | European Pat. Off. . |

OTHER PUBLICATIONS

Wang et al., J. of Biotech., vol. 13, pp. 131–144 (1990).
Wagenback et al., Biotechnology, vol. 9, pp. 57–61 (Jan. 1991).
Smith et al., J. Biol. Chem., vol. 265, No. 22, pp. 13335–13343 (1990).
Loprasert et al., J. Bacteriology, vol. 171, No. 9, pp. 4871–4875 (1989).
Ortlepp et al., J. Biotech., vol. 11, pp. 353–364 (1989).
Saloheimo et al., Gene, vol. 85, pp. 343–351 (1989).
Liao et al., Proc. Nat'l Acad. Sci., vol. 84, pp. 8520–8524 (1987).
Bellino et al. 1985 Biochem Biophys Res Commun 127: 232–238.

*Primary Examiner*—Vasu S. Jagannathan
*Assistant Examiner*—Karen Cochrane Carlson
*Attorney, Agent, or Firm*—Steve T. Zelson, Esq.; Elias J. Lambiris, Esq.

[57] ABSTRACT

Process for producing an extracellular heme protein in increased yields, the process comprising culturing an apoprotein producing microorganism in a fermentation medium containing heme or a heme-containing material under conditions permitting the production of active, recombined heme protein, and recovering the resulting heme protein from the culture medium.

17 Claims, 1 Drawing Sheet

PROCESS FOR PRODUCING HEME PROTEINS

FIELD OF INVENTION

The present invention relates to a process for producing heme proteins in increased yields.

BACKGROUND OF THE INVENTION

The cloning and expression of varius heme proteins in bacteria has previously been described. Thus, S. A. Ortlepp et al., *J. Biotechn.* 11, 1989, pp. 353–364, describe the expression and characterisation of horseradish peroxidase C in *E. coli*. The enzyme is expressed intracellularly as an insoluble aggregate so that it has to be purified from lysed cells. Furthermore, the enzyme is not expressed in active form and must be folded separately in the presence of heme and $Ca^{2+}$ to become functional. Similarly, A. T. Smith et al., *J. Biol. Chem.* 295(22), 1990, pp. 13335–13343, describe the expression of horseradish peroxidase C in *E. coli*. The recombinant enzyme has less activity than native horseradish peroxidase C and is produced in a yield of 2–3% (of the purified, active enzyme). S. Loprasert et al., *J. Bact.* 171(9), 1989, pp. 4871–4875, report the cloning and expression in *E. coli* of peroxidase A from *Bacillus stearothermophilus*. S. J. Hoffman et al., *Proc. Natl. Acad. Sci. U.S.A.* 87, pp. 8521–8525, describe the expression of functional human hemoglobin in *E. coli*. Z. Wang et al., *J. Biotechn.* 13, 1990, pp. 131–144, describe the cloning and expression of lignin peroxidase from *Streptomyces viridosporus* in *Streptomyces lividans*.

Expression of human hemoglobins in yeast (*Saccharomyces cerevisiae*) has been described by M. Wagenbach et al, *Bio/Technology* 9, 1991, pp. 57–61. In yeast, hemoglobin is expressed as a fully assembled, heme-containing tetramer. However, the protein is not secreted from the yeast cells, but remains in the cytoplasmic space and must be purified therefrom.

It would therefore be advantageous to select a host organism, such as a filamentous fungus, which is capable not only of producing heme proteins but also of exporting them through the cell membrane in active form, thereby simplifying purification procedures.

In recent years, procedures have been developed for the transformation of filamentous fungi, including *Aspergillus niger* and *Aspergillus nidulans*. U.S. Pat. No. 4,885,249 (Allelix) describes a general process for the transformation of *A. niger*, exemplified by the introduction of plasmids carrying genes encoding selectable markers. EP 215 594 (Genencor) describes the expression and secretion of various proteins in *A. nidulans*, using the signal sequences of different Aspergillus proteins to provide secretion.

Neither of these references indicates the possibility of producing heme proteins in filamentous fungi. On the contrary, M. Saloheimo et al., *Gene* 85, 1989, pp. 343–351, describe the cloning and expression of a lignin peroxidase from *Phlebia radiata* in *Trichoderma reesei*. The authors report that although lignin peroxidase mRNA is expressed in *T. reesei*, no protein product could be detected. They speculate that this might be ascribable to intracellular degradation by proteases due to incorrect folding of the protein in the absence of heme or to a different structure of the RNA interfering with its translation.

SUMMARY OF THE INVENTION

It has surprisingly been found that when hemin or another material containing heme groups is added to a fermentation medium for growing microorganisms which overproduce the apoprotein of a heme protein, the heme group is bound to the protein whereby the apoprotein is activated and acquires a conformation in which it is more stable against proteolytic degradation. The total yield of heme protein is significantly increased. In this way, endogenous heme synthesis in the host organism, which is often a bottle-neck in the expression of heme proteins, may be overcome.

Accordingly, the present invention relates to a process for producing an extracellular heme protein in increased yields, the process comprising culturing a heme apoprotein producing microorganism in a fermentation medium containing heme or a heme-containing material under conditions permitting the production of active, recombined heme protein, and recovering the resulting heme protein from the medium.

In the present context, the term "heme protein" is intended to include any member of a group of proteins containing heme (e.g. protoporphyrin IX) as a prosthetic group. The term "apoprotein" is intended to indicate a form of the heme protein lacking the prosthetic group. The term "extracellular heme protein" is understood to indicate that unlike the heme proteins provided in the prior art by production in bacteria or yeast, the apoprotein form of the heme protein is secreted from the host cell into the culture mediumwhere it recombines (to the holoprotein) with the prosthetic heme group provided by addition of heme or heme-containing material to the medium.

DETAILED DISCLOSURE OF THE INVENTION

Figure 1:
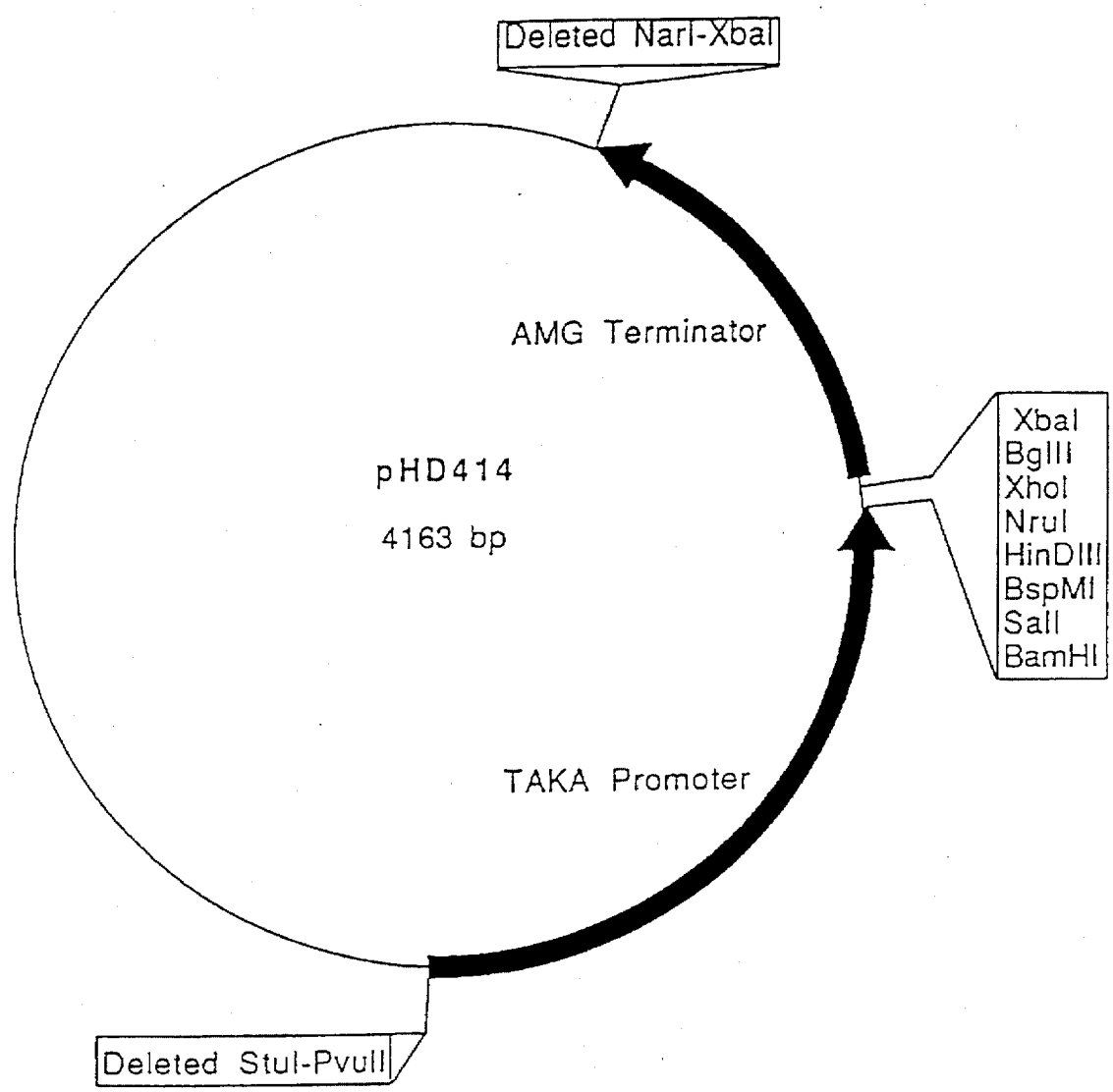
FIG. 1 shows the Aspergillus expression plasmid pHD414 which is a derivative of the plasmid p775.

In a preferred embodiment of the process of the invention, the microorganism producing the heme protein is one transformed with a recombinant expression vector comprising a DNA sequence encoding the heme protein.

Said DNA sequence may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

The DNA sequence may also be of genomic or cDNA origin, for instance obtained by preparing a genomic or cDNA library and screening for DNA sequences coding for all or part of the heme protein by hybridization using synthetic oligonucleotide probes in accordance with standard techniques (cf. Sambrook et al., *Molecular Cloning: A Laboratory Manual*, 2nd Ed., Cold Spring Harbor, 1989). In this case, a genomic or cDNA sequence encoding the heme protein may be modified at a site corresponding to the site(s) at which it is desired to introduce amino acid substitutions, e.g. by site-directed mutagenesis using synthetic oligonucleotides encoding the desired amino acid sequence for homologous recombination in accordance with well-known procedures.

Finally, the DNA sequence may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA sequence in accordance with standard techniques. The DNA sequence may also be prepared by polymerase chain reaction using specific primers, for instance as described in U.S. Pat. No. 4,683,202 or R. K. Saiki et al., Science 239, 1988, pp. 487-491.

Once constructed, the DNA sequence encoding the heme protein is inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the heme protein should be operably connected to a suitable promoter and terminator sequence. The promoter may be any DNA sequence which shows transcriptional activity in the host cell of choice and may be derived from genes encoding proteins either homologous or heterologous to the host cell. When the host cell is a filamentous fungus, the promoter may be derived from a gene encoding an extracellular or intracellular protein such as an amylase, a glucoamylase, a protease, a lipase, a cellulase or a glycolytic enzyme. Examples of suitable promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease or *A. oryzae* triose phosphate isomerase. Terminator sequences may be derived from the same sources as the promoter.

For extracellular expression, the DNA sequence encoding the heme protein is preferably preceded by a signal sequence which may be derived from a gene coding for a secreted protein. Thus, the signal sequence may conveniently be derived from the gene encoding *A. oryzae* TAKA amylase, *A. niger* neutral α-amylase, *A. niger* acid-stable α-amylase, *A. niger* glucoamylase, or a *Coprinus macrorhizus* or cinereus peroxidase.

The procedures used to ligate the DNA sequences coding for the heme protein, the promoter, the terminator and optionally the signal sequence, respectively, and to insert them into suitable vectors are well known to persons skilled in the art (cf., for instance, Sambrook et al., op.cit.).

The microorganism transformed with the recombinant expression vector may be homologous (i.e. the gene is transformed back into the organism from which it was originally derived) or heterologous to the heme protein. It is preferably a fungus, in particular a filamentous fungus such as a fungus belonging to the groups Phycomycetes, Zygomycetes, Ascomycetes, Basidiomycetes or fungi imperfecti, icluding Hyphomycetes such as the genera Aspergillus, Trichoderma, Penicillium, Fusarium or Humicola. The filamentous fungus host organism may conveniently be one which has previously been used as a host for producing recombinant proteins, e.g. a strain of Aspergillus sp., such as *A. niger, A. nidulans* or *A. oryzae*. The use of *A. oryzae* in the production of recombinant proteins is extensively described in, e.g. EP 238 023.

The heme protein produced by the process of the present invention is preferably an oxidoreductase, in particular a peroxidase, including a lignin peroxidase or Mn-peroxidase, or haloperoxidase. In a currently preferred embodiment, the DNA sequence encoding the peroxidase is derived from a *Coprinus* sp., in particular *Coprinus macrorhizus* or cinereus, or *Arthromyces ramosus*. The heme protein may also be a catalase, e.g. a catalase derived from *Aspergillus niger*.

The medium used to culture the transformed host cells may be any conventional medium suitable for growing the host organism in question. The heme or heme-containing material added to the medium to obtain recombination of the secreted apoprotein with the heme group may suitably be supplied by the addition of hemin or, preferably, hemoglobin or red blood cells as the heme group remains functional on heating, permitting autoclaving of media containing one of these substances. When hemin is added to the fermentation medium, it may suitably be present in an amount of 1-1000 mg/l, in particular 10-100 mg/l. When hemoglobin is added to the medium, it may suitably be present in an amount of 0.5-50 g/l, in particular 1-25 g/l. When red blood cells are added to the medium, they may suitably be present in an amount of 0.5-50 g/l, in particular 1-25 g/l.

It has been found that the presence of a surface-active agent in the fermentation medium results in an increased yield of heme protein, currently ascribed to the ability of surface-active agents to stabilise the protein. Consequently, it is preferred to add a surface-active agent, such as Triton X-100, (a polyoxyethylene polymer), polyethylene glycol, or Glanapon (a polymer of polyethylene oxide with side chains of fatty acids), to the medium, e.g. in an amount of 1-100 ml/l.

The invention is further illustrated in the following examples which are not in any way to be construed as limiting to the scope of the invention as claimed.

EXAMPLE 1

Cloning of eDNA encoding a *Coprinus cinereus* peroxidase

Construction of a probe by PCR

Peroxidase cDNA fragments were prepared by polymerase chain reaction (PCR) using specific oligonucleotide primers (R. K. Saiki et al., Science 239, 1988, pp. 487-491) constructed on the basis of the amino acid sequence of the *Coprinus macrorhizus* peroxidase. PCR was carried out using the Gene Amp kit and apparatus (available from Perkin Elmer Cetus, Norwalk, Conn., U.S.A.) in accordance with the manufacturer's instructions, with the exception that the reaction was conducted at 28° C. for the first three cycles in order to obtain better hybridisation to the first strand cDNA (prepared from mRNA obtained from *Coprinus cenereus*, IFO 8371) and subsequently at 65° C. for 30 cycles of PCR.

The following specific primers were used for PCR:

```
                    T  T
1. 5'-GCGCGAATTCGTNGGNATNAACCACGG-3' (SEQ ID NO:1)

A  A
2. 3'-TACAGNTTGACGGGNGGCCTAGGCG-5' (SEQ ID NO:2)

A   T T
3. 5'-GCGAATTCACNCCNCAGGTNTTCGACAC-3' (SEQ ID NO:3)

A   T  A
4. 3'-GGNAAGGGNCCNCTCAAGCCTAGGCG-5' (SEQ IS NO:4)

A
5. 5'-GCGCGAATTCTGGCAGTCNAC-3' (SEQ ID NO:5)

A
6. 5'-GCGCGAATTCTGGCAGAGNATG-3' (SEQ ID NO:6)

T
7. 3'-CGNTACCGNTTCTACAGCCTAGG-5' (SEQ ID NO:7)
```

"N" denoting a mixture of all four nucleotides.

The primers were combined as follows: 1 with 2, 3 with 4, 5 with 7, 6 with 7, 1 with 4, 1 with 7 and 3 with 7. The PCR fragments were thus extended with an EcoRI site at the 5'-end and a BamHI site at the 3'-end. The PCR reactions were analysed on a 1% agarose gel. Bands of the expected size were found in all reactions. To verify that the bands corresponded to peroxidase-specific sequences, the gel was subjected to Southern blotting and hybridised to an oligonucleotide probe with the following sequence

```
       T  A  A  A T
5'-GTCTCGATGTAGAACTG-3' (SEQ ID NO:8)
       T
``` which is positioned between PCR primers 3 and 4. The probe was found to hybridise to bands of approximately 130 bp, 420 bp, 540 bp and 240 bp, thus confimrming that the DNA bands observed correspond to peroxidase sequences.

DNA from the various PCR reactions was digested with EcoRI and BamHI and cloned into the plasmid pUC19 (C. Yanisch-Perron et al., Gene 33, 1985, pp. 103–119). Colonies containing the correct PCR fragments were identified by hybridisation using the oligonucleotide probe specified above. DNA from positive colonies was analysed by restriction enzyme mapping and partial DNA sequence analysis as described by Sanger et al., Proc. Natl. Acad. Sci. U.S.A. 74, 1977, pp. 5463–5467. A 430 bp fragment from one of the clones, obtained by using primer 1 and 4, was used to screen a *Coprinus cinereus* cDNA library as described below.

Construction of a Coprinus cinereus cDNA library in E. coli

Total RNA was extracted from homogenized *Coprinus cinereus* (IFO 8371) mycelium, collected at the time for maximum activity of the peroxidase by methods as described by Boel et al. (EMBO J., 3: 1097–1102, 1984) and Chirgwin et al. (Biochemistry (Wash), 18: 5294–5299, 1979). Poly(A)-containing RNA is obtained by two cycles of affinity chromatography on oligo(dT)-cellulose as described by Aviv and Leder (PNAS, U.S.A. 69: 1408–1412, 1972). cDNA is synthesized by means of a cDNA synthesis kit from Invitrogen according to the manufacturer's instructions. About 50,000 *E. coli* recombinants from the *Coprinus cinereus* cDNA library were transferred to Whatman 540 paper filters. The colonies were lysed and immobilized as described by Gergen et al. (Nucleic Acids Res. 7, 2115–2135, 1979). The filters were hybridized with the $^{32}$P-labelled 430 bp peroxidase-specific probe in 0.2 × SSC, 0.1% SDS. Hybridization and washing of the filters was conducted at 65° C. followed by autoradiography for 24 hours with an intensifier screen. After autoradiography, the filters were washed at increasing temperatures followed by autoradiography for 24 hours with an intensifier screen. In this way, more than 50 positive clones were identified. Miniprep plasmid DNA was isolated from hybridizing colonies by standard procedures (Birnboim and Doly Nucleic Acids Res. 7, 1513–1523, 1979), and the DNA sequence of the cDNA insert was determined by the Sanger dideoxy procedure (Sanger et al., Proc. Natl. Acad. Sci. U.S.A. 74, 1977, pp. 5463–5467). The peroxidase cDNA fragment was exised from the vector by cleavage with HindIII/XhoI and was purified by agarose gel electrophoresis, electroeluted and made ready for ligation reactions. The cDNA fragment was ligated to HindIII/XhoI digested pHD414 to generate pCip in which the cDNA is under transcriptional control of the TAKA promotor from *Aspergillus oryzae* and the AMG terminator from *Aspergillus niger*.

Construction of the Aspergillus expression vector pHD414

The vector pHD414 is a derivative of the plasmid p775 (described in EP 238 023). In contrast to p775, pHD414 has a string of unique restriction sites between the promotor and the terminator.

The plasmid was constructed by removal of an approximately 200 bp long fragment (containing undesirable restriction sites) at the 3' end of the terminator, and subsequent removal of an approximately 250 bp long fragment at the 5' end of the promotor, also containing undesirable restriction sites. The 200 bp region was removed from p775 by cleavage with NarI (positioned in the pUC vector) and XbaI (positioned just 3' to the terminator), subsequent filling in the generated ends with Klenow DNA polymerase +dNTP, purification of the vector fragment on gel and religation of the vector fragment. The DNA was transformed into *E. coli* MC1061 as described above. 10 colonies (pHD413-1 to -10) were selected and analyzed by restriction enzyme analysis. One of the clones exhibiting the expected band pattern in the restriction enzyme analysis was used in the construction of pHD414.

pHD413 was cut with StuI (positioned in the 5' end of the promoter) and PvuII (positioned in the pUC vector) and fractionated on a gel. The vector fragment was purified, religated and transformed into *E. coli* MC1061.12 colonies were selected and analyzed by restriction enzyme analysis. All 12 clones exhibited the expected band pattern. The plasmid pHD414 is shown in FIG. 1.

Transformation of *Aspergillus oryzae* or *Aspergillus niger* (general procedure)

100 ml of YPD medium (Sherman et al., Methods in Yeast Genetics, Cold Spring Harbor Laboratory, 1981) was inoculated with spores of *A. oryzae* or *A. niger* and incubated with shaking at 37° C. for about 2 days. The mycelium was harvested by filtration through miracloth and washed with 200 ml of 0.6M MgSO$_4$. The mycelium was suspended in 15 ml of 1.2M MgSO$_4$. 10 mM NaH$_2$PO$_4$, pH=5.8. The suspension was cooled on ice, and 1 ml of buffer containing 120 mg of Novozym® 234, batch 1687 was added. After 5 minutes 1 ml of 12 mg/ml BSA (Sigma type H25) was added, and incubation with gentle agitation was continued for 1.5–2.5 hours at 37° C. until a large number of protoplasts was visible in a sample inspected under the microscope.

The suspension was filtered through miracloth, the filtrate was transferred to a sterile tube and overlayered with 5 ml of 0.6M sorbitol, 100 mM Tris-HCl, pH=7.0. Centrifugation was performed for 15 minutes at 100 g, and protoplasts were collected from the top of the $MgSO_4$ cushion. 2 volumes of STC (1.2M sorbitol, 10 mM Tris-HCl, pH=7.5. 10 mM $CaCl_2$) were added to the protoplast suspension and the mixture was centrifuged for 5 minutes at 1000 × g. The protoplast pellet was resuspended in 3 ml of STC and repelleted. This procedure was repeated. Finally the protoplasts were resuspended in 0.2–1 ml of STC.

100 µl of the protoplast suspension was mixed with 5–25 µg of the appropriate DNA in 10 µl of STC. Protoplasts from the argB strains were mixed with pSa143 DNA (an *A. nidulans* argB gene carrying plasmid) and protoplasts from the argB$^+$ strains were mixed with p3SR2 (an *A. nidulans* amdS gene carrying plasmid). The mixture was left at room temperature for 25 minutes. 0.2 ml of 60% PEG 4000 (BDH 29576), 10 mM $CaCl_2$ and 10 mM Tris-HCl, pH =7.5, were added and carefully mixed (twice) and finally 0.85 ml of the same solution was added and carefully mixed. The mixture was left at room temperature for 25 minutes, spun at 2500 × g for 15 minutes and the pellet was resuspended in 2 ml of 1.2M sorbitol. After another sedimentation, the protoplasts were spread on the appropriate plates. Protoplasts from the argB strains transformed with pSa143 were spread on minimal plates (Cove Biochem.Biophys.Acta 113 (1966) 51–56) with glucose and urea as carbon and nitrogen sources, respectively, and containing 1.2M sorbitol for osmotic stabilization. Protoplasts from the argB-strains transformed with p3SR2 were spread on minimal plates (Cove Biochem.Biophys.Acta 113 (1966) 51–56) containing 1.0M sucrose, pH=7.0, 10mM acetamide as nitrogen source and 20 mM CsCl to inhibit background growth. After incubation for 4–7 days at 37° C. spores were picked, suspended in sterile water and spread for single colonies. This procedure was repeated and spores of a single colony after the second reisolation were stored as defined transformants.

EXAMPLE 2

Production of recombinant Coprinus cinereus peroxidase in an *A. oryzae* strain in a fermentation medium containing hemin pCip was transformed into *A. oryzae* A1560 (IFO 4177) by cotransformation with p3SR2 containing the amdS gene from *A. nidulans* as described above with a mixture of equal amounts of pCip and p3SR2 (approximately 5 µg of each). Transformants which are able to use acetamide as their sole nitrogen source were reisolated twice.

300 ml propylene shake flasks containing 50 ml ASP03 medium with the following composition

| | |
|---|---|
| Yeast extract | 1 g/l |
| Succinic acid | 10 g/l |
| $MgCl_2.6H_2O$ | 0.82 g/l |
| KCl | 1.83 g/l |
| $NaH_2PO_4.2H_2O$ | 1.01 g/l |
| $NaSO_4$ | 1.8 g/l |
| Urea | 2 g/l |
| Citric acid | 2 g/l |
| Trace metal solution | 0.5 ml/l |
| Pluronic | 0.1 ml/l |
| Water up to | 1000 ml |
| pH adjusted to 6.00 with NaOH | | which had been autoclaved at 121° C. for 60 min. followed by addition of 20 g/l of maltodextrin and varying amounts of hemin (Sigma H-2250) dissolved in 0.01M NaOH and sterile filtered into the flasks through a 0.2 µm membrane (pH 12), were inoculated with 1 ml of a spore suspension (approximately $10^6$ spores/ml) of *A. oryzae* transformants and incubated at 34° C. for 72 hours at 300 rpm.

The results are shown in the table below. Peroxidase activity was measured in PODU/ml. (1 PODU (peroxidase unit) is defined as the amount of enzyme that catalyses the conversion of 1 µmol $H_2O_2$ per minute in a system where 2,2'-azinobis[3-ethylbenzothiazoline-6-sulfonate] is oxidised in the presence of 1 mM $H_2O_2$, pH 7.0, at a temperature of 25° C.)

| Hemin conc. in in the medium | Peroxidase activity after 72 hours. |
|---|---|
| 0 mg/l | 300 PODU/ml |
| 1 — | 360 — |
| 10 — | 680 — |
| 100 — | 1000 — |
| 1000 — | 1029 — |

It appears from the table that addition of hemin to the growth medium significantly increases the peroxidase yield.

EXAMPLE 3

Production of recombinant Coprinus cinereus peroxidase in an *A. oryzae* strain in a fermentation medium containing hemin and a surface-active agent

*A. oryzae* transformants obtained as described above were cultured as described in Example 2 in a medium to which Glanapon DG 160 (available from Bussetti) had been added as a surface-active agent before autoclaving. The results appear from the table below.

| Heme conc. | Glanapon conc. | POD act. after 72 hours. |
|---|---|---|
| 0 mg/l | 0 ml/l | 300 PODU/ml |
| 1 — | 0 — | 360 — |
| 10 — | 0 — | 680 — |
| 0 — | 5 — | 380 — |
| 1 — | 5 — | 521 — |
| 10 — | 5 — | 1480 — |

It appears from the table that the added Glanapon has an excellent synergistic effect with hemin on the peroxidase yield.

EXAMPLE 4

Production of recombinant Coprinus cinereus peroxidase in an *A. oryzae* strain in a fermentation medium containing hemin, hemoglobin or red blood cells

*A. oryzae* transformants obtained as described above were cultured as described in Example 2 in a medium to which hemin, hemoglobin (Merck Art 4300) or red blood cells (spray-dried mixed porcine and bovine red blood cells, food grade) has been added (before or after autoclaving). Hemoglobin and red blood cells were dissolved at pH 10.5 (NaOH) before autoclaving and sterile filtration. The results appear from the table below.

| | Peroxidase activity after 72 hours | |
|---|---|---|
| Heme source | Sterile filtered | Autoclaved 20 min. 121° C. |
| Hemin (10 mg/l) | 800 PODU/ml | 448 PODU/ml |
| Hemoglobin | 1020 — | 958 — |
| Red blood cells (1 g/l) | | 903 — |

It appears from the table that heme sources, where the heme group is bound to globin results in a significant increase in the peroxidase yield. A further advantage is that they can be obtained very cheaply and that the heme group is protected against destruction during heat sterilisation.

EXAMPLE 5

Production of recombinant Coprinus cinereus peroxidase in an *A. oryzae* strain in a 2 liter fermentor in a fermentation medium containing hemoglobin

*A. oryzae* transformants obtained as described above were fermented in 2 liter laboratory fermentors in a fed batch process as follows:

| Tank medium: | $MgSO_{4 \cdot 7H_2O}$ | 2 g/l |
|---|---|---|
| | KH2PO4 | 2 g/l |
| | K2SO4 | 3 g/l |
| | Citric acid | 4 g/l |
| | Trace metals | |
| | Yeast extract | 1 g/l |
| | Pluronic | 0,2 ml/l |
| Feed medium: | Maltose | 250 g/l |
| | Yeast extract | 7 g/l |
| | FeSO4.7H2O | 1 g/l |
| | Urea | 20 g/l |

| Fermentation conditions: | Pluronic 2 ml/l |
|---|---|
| | 2,0 l fermentors |
| | Temp. 34° C. |
| | pH = 7.8 |
| | pO2 > 20% by increasing agitation speed. |
| | aeration: 1VVM |
| | Feed profile: 3 g/l × h 0–24 hours. |
| | 6 g/l × h 24–144 - . |
| | Inoculated with 50 ml 24 hour-old ASP03 shake flask culture. |

During sterilisation the pH was increased to 10.5 for tank medium and/or feed medium (if supplied with hemoglobin). The hemoglobin was autoclaved at 121° C. for 40 min. at pH 10.5. Before fermentation, the pH was adjusted to 7,8.

The results appear from the table below.

| Fermentation no. | Conc of hemoglobin in | | Peroxidase yield after 144 hours (in %)* |
|---|---|---|---|
| | tank medium | feed medium | |
| 74 | 0 g/l | 0 g/l | 100 |
| 78 | 1 g/l | 0 g/l | 117 |
| 79 | 5 g/l | 5 g/l | 250 |
| 115 | (red blood cells) 5 g/l | 10 g/l | 300 |
| 26 | (hemin sterile filtr.) 50 mg/l | | 117 |

*The yield of peroxidase in medium without added hemoglobin is arbitrarily set at 100%

It appears from the table that the yield of peroxidase can be increased significantly by adding hemoglobin to the fermentation medium. It have not been possible to obtain the same degree of yield increase with hemin.

I claim:

1. A process for producing an extracellular heme protein in increased yields, the process comprising:
 (a) culturing an apoprotein producing microorganism in a fermentation medium containing heme or a heme-containing material under conditions where heme is incorporated into the apoprotein and;
 (b) recovering the resulting heme protein from the medium.

2. A process according to claim 1, wherein the microorganism is transformed with a recombinant expression vector comprising a DNA sequence encoding a heme protein.

3. A process according to claim 2, wherein the DNA sequence encodes a heterologous heme protein.

4. A process according to claim 1, wherein the microorganism is a fungus.

5. A process according to claim 4, wherein the fungus is a filamentous fungus.

6. A process according to claim 5, wherein the filamentous fungus is a strain of Aspergillus.

7. A process according to any of claim 1, wherein the heme protein is an oxidoreductase or a catalase.

8. A process according to claim 7, wherein the oxidoreductase is a peroxidase or a haloperoxidase.

9. A process according to claim 8 wherein the peroxidase is derived from a species of Coprinus, e.g. *Coprinus macrorhizus* or *Coprinus cinereus,* or Arthrmyces.

10. A process according to any of claim 1, wherein the heme-containing material is hemoglobin or red blood cells.

11. A process according to claim 1, wherein the fermentation medium contains hemin in an amount of 1–1000 mg/l.

12. The process of claim 11 wherein the fermentation medium contains hemin in an amount of 10–100 mg/l.

13. A process according to claim 10, wherein the fermentation medium contains hemoglobin in an amount of 0.5–50 g/l.

14. The process according to claim 10, wherein the fermentation medium contains hemoglobin in the amount 1–25 g/l.

15. A process according to claim 10, wherein the fermentation medium contains red blood cells in an amount of 0.5–50 g/l.

16. A process according to claim 1, wherein the fermentation medium additionally contains a surface active agent.

17. A process according to claim 1, wherein the fermentation medium contains the surface-active agent in an amount of 1–100 ml/l.

\* \* \* \* \*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:1:

GCGCGAATTC GTGGATACCA CGG       2 3

( 2 ) INFORMATION FOR SEQ ID NO:2:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:2:

GCGGATCCGG GGGCAGTGAC AT    22

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GCGAATTCAC CCCAGGTTTA CAC    23

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GCGGATCCGA ACTCCCGGGA AGG    23

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GCGCGAATTC TGCAGTCAC    19

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GCGCGAATTC TGGCAGAATG    20

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GGATCCGACA TCTTGCCATG C    21

( 2 ) INFORMATION FOR SEQ ID NO:8:

( i ) SEQUENCE CHARACTERISTICS:
  ( A ) LENGTH: 11 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:8:

GTTATTAAAT G       1 1